United States Patent [19]
Gilliland et al.

[11] Patent Number: 5,297,420
[45] Date of Patent: Mar. 29, 1994

[54] APPARATUS AND METHOD FOR MEASURING RELATIVE PERMEABILITY AND CAPILLARY PRESSURE OF POROUS ROCK

[75] Inventors: Ronnie E. Gilliland, New Orleans, La.; Daniel R. Maloney, Bartlesville, Okla.

[73] Assignee: Mobil Oil Corporation, Fairfax, Va.

[21] Appl. No.: 64,390

[22] Filed: May 19, 1993

[51] Int. Cl.$^5$ ............................................. G01N 15/08
[52] U.S. Cl. ....................................................... 73/38
[58] Field of Search ............................. 73/38; 324/376

[56] References Cited

U.S. PATENT DOCUMENTS

| | | | |
|---|---|---|---|
| 2,534,718 | 12/1950 | Leas et al. | 73/38 |
| 4,543,821 | 10/1985 | Davis, Jr. | 73/38 X |
| 4,649,483 | 3/1987 | Dixon, Jr. | 364/422 |
| 4,669,299 | 6/1987 | Closmann | 73/38 |
| 4,868,751 | 9/1989 | Dogru et al. | 364/422 |
| 4,907,448 | 3/1990 | Givens | 73/153 |
| 4,926,128 | 5/1990 | Givens | 324/376 |
| 5,063,509 | 11/1991 | Coles et al. | 364/420 |
| 5,069,065 | 12/1991 | Sprunt et al. | 73/153 |
| 5,079,948 | 1/1992 | Collins et al. | 73/153 |
| 5,086,643 | 2/1992 | Marek | 73/38 |
| 5,095,273 | 3/1992 | Kennedy et al. | 324/376 |
| 5,209,104 | 5/1993 | Collins et al. | 73/38 |

Primary Examiner—Hezron E. Williams
Assistant Examiner—Joseph W. Roskos
Attorney, Agent, or Firm—Alexander J. McKillop; George W. Hager, Jr.

[57] ABSTRACT

A core sample of a porous rock from a subterranean reservoir is placed in a pressure cell holder. The sample is desaturated to first fluid irreducible desaturation with a second fluid through a porous plate preferentially wet to only the first fluid. The sample is then flooded with a plurality of first and second fluid ratios. Core pressure is measured along the core at various differential pressure plateau's during initial first fluid desaturation and again during fluid flooding with first and second fluids. A computed tomography (CT) scanning system provides images of the density distribution within the core sample during such flooding. Fluid saturation, determined from these CT images, and the pressure measurements are used to determine the relative permeability and capillary pressure responses of the fluids within the subterranean reservoir.

11 Claims, 2 Drawing Sheets

APPARATUS AND METHOD FOR MEASURING RELATIVE PERMEABILITY AND CAPILLARY PRESSURE OF POROUS ROCK

BACKGROUND OF THE INVENTION

In the production of minerals, e.g., oil and gas, certain properties of a subterranean reservoir must be determined. One of the most important of these properties is the permeability of the reservoir. Permeability of a material is a measure of the ability of the material to transmit fluids through its pore spaces and is inversely proportional to the flow resistance offered by the material. Normally, permeability is determined by taking core samples from the reservoir and carrying out well-defined measurement techniques on the samples. There are several techniques available for making such measurements, many of which are described in PETROLEUM PRODUCTION ENGINEERING DEVELOPMENT by L. C. Uren, Fourth Edition, McGraw-Hill Book Company, Inc., 1956, pps. 660-669. Another standard reference is American Petroleum Institute, API RECOMMENDED PRACTICE FOR CORE-ANALYSIS PROCEDURE, API RP40, 1960.

In addition to these well known techniques, a more recently applied technique involves the use of computed tomography (CT) technology. CT technology has been used in the medical field for several years. CT scanning instruments produce a cross-sectional view through the subject material along any chosen axis. The advantages of CT scanning over conventional radiography is found in its ability to display the electron density variations within the object scanned in a two-dimensional X-ray image.

More recently, CT scanning technology has been applied to the field of energy research for examining the interior of stationary or slowly changing earth materials, such as coal, shale and drilling cores. Processes involved in coal gasification and combustion have been monitored using time-lapse CT imagery to observe changes in density (e.g. thermal expansion, fracturing, emission of gases, consumption by combustion and the like) during progressive heating in a controlled atmosphere. Core flooding experiments can now be carried out with CT scanning to aid in enhanced oil recovery and fluid mobility control. For example, the permeability of materials within core samples to various fluids at varying conditions of temperature and pressure can be determined. Such experiments involve flushing a fluid through a core sample and monitoring the shape of the fluid fronts. By subtracting the images of the cores before and after flooding, the exact shape of the fluid front is determined. Such core flooding experiments allow the interior of the core sample to be observed without disturbing the sample. The sweep efficiency and flow paths of fluids of interest may now be studied on the scale of millimeters. The penetration of X-rays allows experiments to be performed with up to four-inch diameter cores samples.

Drilling fluids can be analyzed by CT scanning as such fluids are characterized by high-density brines, various organics and several compositionally different weighting agents. Formation damage can be investigated since CT scanning can detect migration of clays, absorption of organics and the reversibility of completion fluid penetration. Shale oil recovery can also be aided as CT scanning could detect penetration by solvents and could directly measure structure changes on retorting.

U.S. Pat. No. 4,649,483, issued to Dixon, discloses a method for determining fluid saturation in a porous media through the use of CT scanning. Multi-phase fluid saturation in a sample of porous media is determined through computer tomographic scanning. The sample is scanned with X-rays of differing energies in both the fluid saturated and the fluid extracted states. Each of the extracted fluids is also scanned at differing X-ray energies. The computed tomographic images produced are utilized in the determination of the X-ray mass attenuation coefficients for the sample and the extracted fluids. From these mass attenuation coefficients, the weight fractions and volume fractions of each of the extracted fluids are determined.

U.S. Pat. No. 4,688,238, issued to Sprunt et al. discloses a method for using CT scanning over a range of confining pressures on a core sample to determine pore volume change, pore compressibility and core fracturing. A core sample with a surrounding elastic jacket is placed in a confining pressure cell. Pressure is applied to the cell to press the jacket into contact with the surface of the sample. The pressure in the cell is increased stepwise over a plurality of pressure points. The sample is scanned at a plurality of locations with X-rays at each of the pressure points. Computed tomographic images of the sample are produced for each of the X-ray scans. The conformance of the jacket to the sample is determined from these computed tomographic images. From such conformance, a range of confining pressures is determined over which pore volume and pore compressibility of the sample are measured without being affected by improper conformance of the jacket to the surface of the sample. Also rock fracturing is determined from the pressure at which crushing of the sample destroys permeable channels within the sample and results in a permeability measurement that is lower than the actual permeability measurement.

Relative permeability plays a very important role in describing the fluid flow in oil and gas reservoirs. Two methods of measurement are practiced by industry; namely, steady-state and dynamic displacement. In each method a cylindrical core is saturated with water or brine, then oil flooded to irreducible water saturation. Subsequently, the core is water flooded or brine flooded and the pressure drop across the core is measured along with the oil and water or brine production. The average saturations within the core are determined from the overall material balance. The steady-state method requires lengthy measurement times because it requires stabilization of the fluid flow. The dynamic displacement method overcomes this, however, it suffers from capillary end effects. Hence the displacement method is generally only effective for high flow rates.

U.S. Pat. No. 4,672,840, issued to Cullick, discloses a method and system for determining fluid volumes of a two-phase effluent flow through a porous material in order to determine permeability characteristics. A two-phase flow condition is established through the porous material, such as a core sample taken from a subterranean hydrocarbon-bearing reservoir. One phase is a liquid hydrocarbon phase, the other an insoluble displacing liquid phase. After exiting the core sample, the two-phase fluid is collected in a container where it separates into an overlying fluid phase, such as an oil phase, and an underlying fluid phase, such as a water phase. A fluid level monitor is positioned in the container. When the air-fluid interface at the top of the overlying fluid phase rises to a first position in the upper portion of the container, drainage of the underlying fluid phase is initiated. The time is measured during which the fluid-fluid interface of the overlying and underlying fluid phases is lowered to a second position near the bottom of the container. The time is also measured during which the air-water interface of the top of the overlying fluid phase is lowered to the same second position near the bottom of the container. The volumes of each of the two fluid phases are determinable from the time measurements and the drainage flow rate of the fluid, such volumes being representative of fluid saturation in the core sample from which core sample permeability is thus determined.

U.S. Pat. No. 4,868,751, issued to Dogru et al., relates to a method for determining relative permeability of a core sample taken from a subterranean hydrocarbon-bearing reservoir. In the method disclosed therein pressure and fluid saturation are measured at a plurality of corresponding positions along the core before and during fluid flooding of the core. From these measurements the relative permeability of the reservoir is determined. At the start of the relative permeability measurement, the core is fully saturated with a known weight or volume of a saturating fluid, such as an oil or a brine. Dual energy X-ray CT scans are taken at a plurality of scan positions. Thereafter, the core saturation is altered through the core by flowing a displacing fluid, other than that with which the core is saturated, such as an oil, water or brine, and both saturation and pressure measurements made.

In desaturating the core sample to a state of irreducible saturation of the first fluid, dynamic displacement is often insufficient. This problem is especially acute in the case of gas displacing brine or water, since the viscosities and densities of the two fluids are widely disparate and tend to result in an incomplete initial displacement of the water to irreducible saturation. The sample must often be removed and the desaturation process completed with centrifugal force or by differential pressure across a preferentially water wet porous plate, then returned to the test apparatus for resumption of the experiment. The apparatus and method of the present invention allow the desaturation of the water-saturated sample through a preferentially water-wet ceramic porous plate during displacement with air or other gas while the sample remains in the relative permeability test apparatus, then routing the flow around the porous plate to allow determination of steady state relative permeability which requires that both fluids flow without restriction. The desaturation may be accomplished in several steps of differential pressure and waiting a sufficient time at each step for pressure and saturation equilibrium to occur. From these data, the capillary pressure response of the sample may be determined. U.S. Pat. No. 5,069,065 to E. S. Sprunt et al. and U.S. Pat. No. 5,079,948 to S. H. Collins et al. describe in detail such porous plate capillary pressure methods. The teachings of such patents are incorporated herein by reference.

It is therefore an object of the present invention to provide a new method and system for determining the relative permeability and capillary pressure of a subterranean reservoir by determining two-phase, steady-rate relative permeability and porous plate capillary pressure response characteristics of core samples obtained from such a reservoir.

SUMMARY OF THE INVENTION

In accordance with the present invention, a core sample of a porous rock is saturated with a first fluid. The saturated core sample is scanned with X-rays and X-ray attenuation measured. The core sample is desaturated to an irreducible first fluid saturation condition by injecting a second fluid into the core sample that is immiscible with the first fluid and displacing the first fluid through a first member that is permeable to the first fluid and impermeable to the second fluid. This desaturation is performed in a series of steps of varying differential pressures as measured by pressure gauges on the inlet and outlet flow connections of the test apparatus. At each step, sufficient waiting time is allowed for the system to reach pressure equilibrium, whereby the noted saturation versus differential pressure performance across the preferentially water permeable ceramic plate is related to capillary pressure characteristics of the core sample. This saturation is measured by scanning the sample using X-ray attenuation measurements at a plurality of points along the axis of the sample. At a point where the increase of differential pressure forcing the displacement of the first fluid through the preferentially permeable first member by injection of the second, immiscible fluid produces no more expulsion of the first fluid, the injection process stops. The sample should then be at a condition of irreducible saturation of the first fluid. Then a flow of the second fluid only is injected and displaces the second fluid in the sample. Pressure and saturation measurements are taken at this point to establish the relative permeability of the second fluid with respect to the first fluid when the first fluid saturation is at irreducible conditions.

Next, a plurality of increasing ratios of first to second fluids are injected to displace the first and second fluids through a second member that is permeable to both the first and second fluids. During this injection and displacement, X-ray scanning is again carried out. Finally, a plurality of decreasing ratios of first to second fluids are injected to displace the first and second fluids through such second member to an irreducible first fluid saturation condition. X-ray scanning is again carried out. During each of the above fluid flooding steps, pressure gradients along the core sample are measured. From these X-ray attenuation and pressure measurements the two-phase, steady-state relative permeability and capillary pressure response of the core sample is determined.

DESCRIPTION OF THE PREFERRED EMBODIMENT

Figure 1:
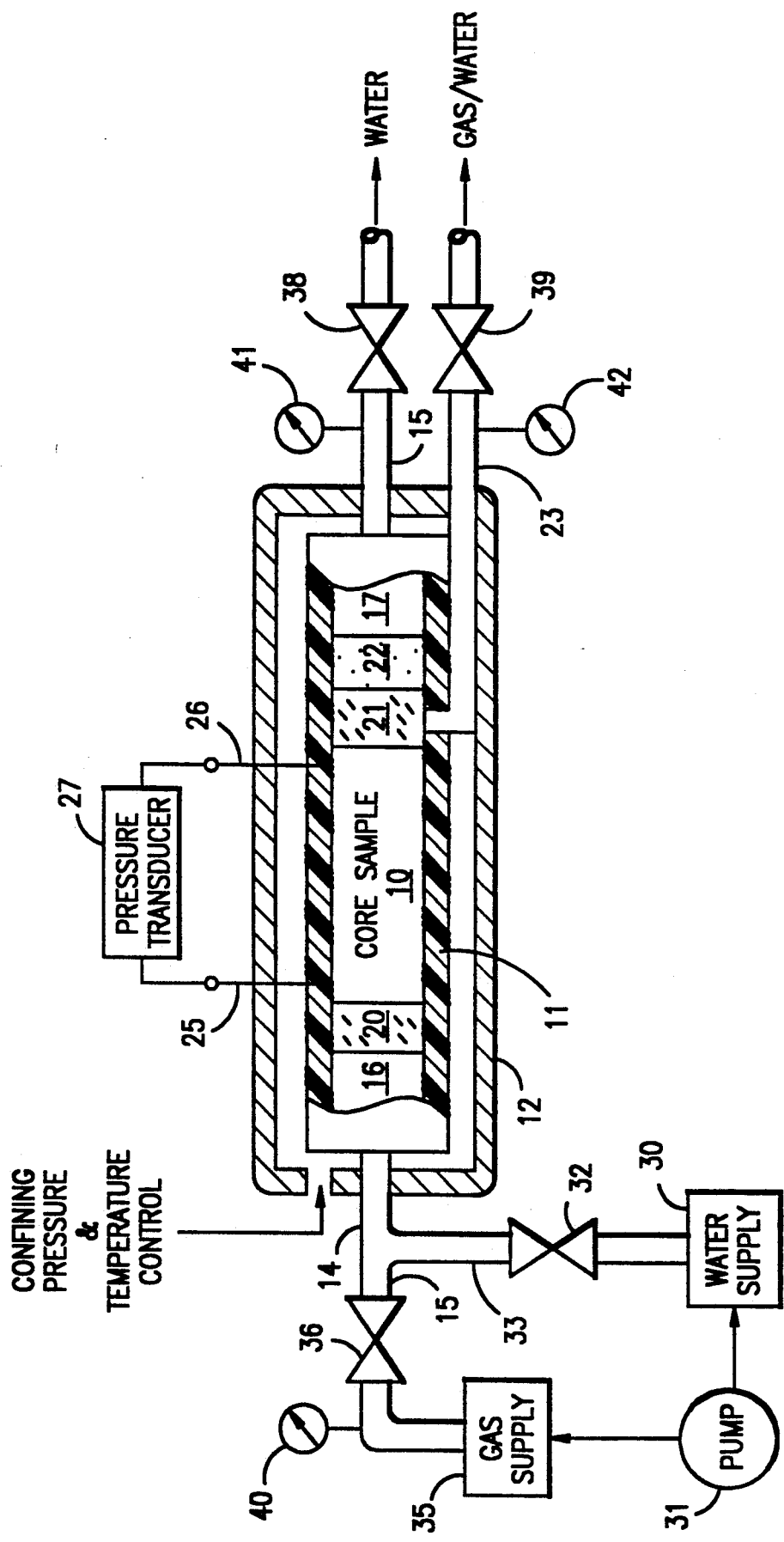
FIG. 1 is a schematic representation of apparatus for carrying out two-phase relative permeability and capillary pressure determinations on a core sample of porous rock from a subterranean reservoir in accordance with the present invention.

Referring to FIG. 1 there is illustrated apparatus for carrying out two-phase, steady-state relative permeability and capillary pressure measurements on porous rock from a subterranean reservoir. A core sample of the porous rock is placed in a pressure sleeve 11, preferably natural or synthetic rubber, which is in the form of a cylinder surrounding the core sample. Sleeve 11 is placed inside a suitable pressure vessel 12 that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al. Through such a pressure vessel a pressure is applied to the sleeve 11 and hence to the core sample 10. A fluid inlet 14 and fluid outlet 15 pass through end plugs 16 and 17 respectively Which are insaturated into the sleeve 11 and also through pressure vessel 12.

Positioned adjacent both ends of core sample 1 are water-and gas-permeable plugs 20 and 21, preferably a Berea sandstone. Positioned between Berea sandstone plug 21 and end plug 17 is a water-permeable and gas-impermeable plug 22, preferably a porous ceramic plate. A fluid outlet 23 passes from Berea sandstone plug 21 through sleeve 11 and pressure vessel 12. Pressure taps 25 and 26 connect a pressure transducer 27 across the core sample 10 so that pressure along the core sample can be monitored.

In carrying out the relative permeability measurements of the present invention, a clean core sample 10 is initially saturated with water or brine flowing from a water supply reservoir 30 under pressure from pump 31 through open valve 32, pipe 33, inlet 14, end plug 16 and Berea sandstone plug 20. Valves 36, 38 and 39 are closed. The Berea sandstone has a higher permeability than the core sample and acts as a mixing header for gas and water and minimizes end effects in saturation of the core sample. It is important that the wettability of the Berea sandstone be the same as that of the core sample so that the relative permeability measurements are not adversely affected. This is not usually a problem in gas/water measurements since a gas/water reservoir is typically assumed to be water wet, as is cleaned Berea sandstone. The saturated core sample is then brought up to reservoir temperature and overburden pressure conditions.

Figure 2:
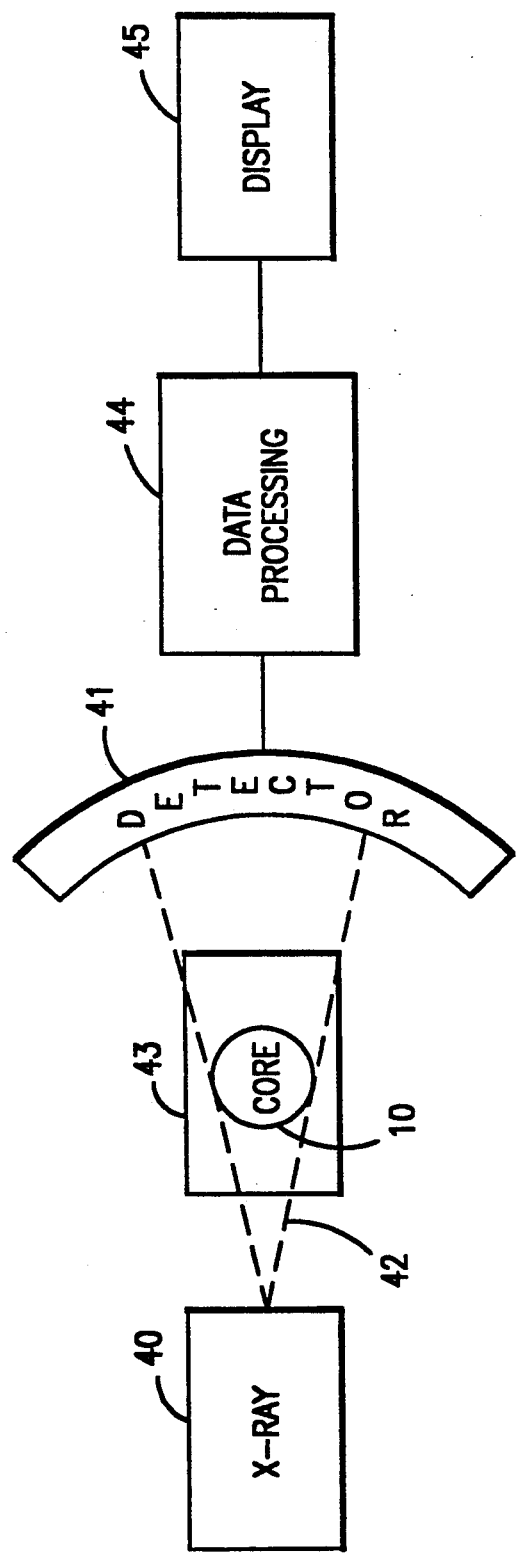
FIG. 2 illustrates a computed tomography system for use with the apparatus of FIG. 1 in carrying out two-phase relative permeability and capillary pressure determinations in accordance with the present invention.

Next, a baseline CT scan of the water-saturated core sample 10 is made with the CT scanning system of FIG. 2. This system produces a display or image of the density distribution in a cross-section or transverse slice of the core. X-ray energy provided by the X-ray tube 40 passes through the pressure housing 12, sleeve 11 and core sample 10 and falls on the detector array 41. Rotation and indexing of core sample 10 within the X-ray fan beam 42 is provided by the gantry 43. After a desired number of scans are completed for each sample slice, the core is indexed to place the next sample slice within the path of the X-ray fan beam 42. Signals from detector array 41 are applied through data processing unit 44 to display 45 where the CT images are viewed. The CT scanning systems of the aforementioned U.S. Pat. Nos. 4,649,483; 4,688,238; 4,672,840 and 4,868,751 are particularly suitable for use in the present invention of determining two-phase, steady-state relative permeability and capillary pressure and their teachings are incorporated herein by reference. The average intensity of the CT images establish CT numbers which are used in accordance with the aforementioned U.S. patents to determine the saturation of each CT scan slice.

Referring again to FIG. 1, the core sample is desaturated to effect a first irreducible water saturation condition by injecting gas from supply reservoir 35 under pressure from pump 31 through open valve 36, pipes 37 and 14 and plugs 16 and 20 into core sample 10 to displace water from the core sample through water and gas permeable plug 21, water permeable plug 22, end plug 17, pipe 15 and open valve 38. Valves 32 and 39 are closed. This desaturation is accomplished in stepwise fashion. The pressure differential between pressure gauges 40 and 41 on inlet line 37 and outlet line 15 designate the capillary pressure acting across water permeable core sample 10. Upon reaching each step in the desaturation process, the system is held static until pressure differential across the system indicated by difference between gauges 40 and 41, and water saturation as measured by CT scan stabilize. Both water saturation and pressure differential are noted for later analysis. If incremental capillary pressure is not desired, the desaturation process can sometimes be accomplished faster by first flowing gas from gas supply 35 as pressured by pump 31 through open valve 36, inlet pipes 37 and 14, and plugs 16 and 20 into core sample 10 to displace water from the core sample 10 through water and gas permeable plug 21, outlet line 23 and open valve 39 to reach a water saturation attainable by viscous flow, then to complete the desaturation process by closing valve 39 and opening valve 38, forcing the remaining water through preferentially water permeable plug 22, outlet line 15 and valve 38. CT scanning is carried out at a plurality of intervals during desaturation to measure X-ray attenuation and thereby monitor water saturation decrease.

Next, a plurality of increasing ratios of water to gas are injected into the core sample from reservoirs 30 and 35 by the controlled opening of valves 32 and 36 to displace water and gas from the core sample through water and gas permeable plug 21, pipe 23 and open valve 39 until a 100% water injection is reached. Valve 38 is closed. CT scanning is again carried out at a plurality of intervals to measure X-ray attenuation and pressure gradient along the core sample is also measured.

Thereafter, a plurality of decreasing ratios of water to gas are injected into the core sample from reservoirs 30 and 35 by the controlled opening of valves 32 and 36 to displace water and gas from the core sample through water and gas permeable plug 21, pipe 23 and open valve 39 until irreducible water saturation attainable by viscous forces is reached. Valve 38 is closed. CT scanning is again carried out at a plurality of intervals to measure X-ray attenuation and pressure gradient along the core sample is also measured.

From the foregoing core sample measurements of X-ray attenuation and pressure, two-phase, steady-state relative permeability and capillary pressure determinations can be made in accordance with the aforementioned U.S. Pat. No. 4,868,751 to Dogru et al., the teachings of which are incorporated herein by reference.

Having now described and illustrated a preferred embodiment of the present invention, it is to be understood that various modifications and alterations may be made without departing from the spirit and scope of the invention as set forth in the appended claims.

I claim:

1. Apparatus for measuring porous rock properties at subterranean reservoir conditions, comprising:
   a) a sleeve containing a core sample of a porous rock saturated with a first fluid,
   b) a fluid inlet positioned in a first end of said sleeve through which a second fluid is injected under pressure into a first end of said core sample for displacing said first fluid from a second end of said core sample, said second fluid being immiscible with said first fluid, c) a first member positioned adjacent a second end of said core sample within said sleeve and which is permeable to said first fluid and impermeable to said second fluid, d) a second member positioned between said first member and the second end of said core sample which is permeable to both said first fluid and said second fluids, e) a first fluid outlet positioned in a second end of said sleeve through which said first fluid flows from said sleeve after having been discharged from the second end of said core sample through said first and second members, f) a second fluid outlet positioned in said second end of said sleeve through which said first and second fluids flow from said sleeve after having been discharged from the second end of said core sample through said second member, g) a first valve positioned in said first fluid outlet for controlling the discharge of said first fluid from said core sample through said first and second members, h) a second valve positioned in said second fluid outlet for controlling the discharge of both said first and second fluids from said core sample through said second member, i) means for applying a confining pressure through said sleeve to said core sample, j) a pair of pressure taps contacting the outer surface of said core sample at spaced-apart positions along the length of the core sample, and k) a pressure transducer connected to said pressure taps for measuring pressure across said core sample.

2. The apparatus of claim 1 wherein said first member is porous.

3. The apparatus of claim 2 wherein said first member is a ceramic plate.

4. The apparatus of claim 1 wherein said second member is sandstone.

5. The apparatus of claim 4 wherein said second member is a Berea sandstone.

6. The apparatus of claim 1 wherein said first fluid is water and said second fluid is a gas.

7. The apparatus of claim 6 wherein said second fluid is nitrogen.

8. The apparatus of claim 7 further including means for measuring the attenuation of X-rays by said core sample.

9. Method for measuring two-phase, steady-state relative permeability of a porous rock at reservoir conditions, comprising the steps of:

a) injecting a first fluid into a core sample of a porous rock to effect a first fluid saturation throughout said porous rock, b) scanning said saturated core sample with X-rays and measuring the attenuation of said X-rays as they pass through said core sample to determine fluid saturation, c) desaturating said core sample to effect a first irreducible first fluid saturation condition by injecting a second fluid into said core sample that is immiscible with said first fluid and displacing said first fluid from said core sample through a first member that is permeable to said first fluid and impermeable to said second fluid, d) repeatedly scanning said core sample with X-rays during step c) and measuring the attenuation of said X-rays as they pass through said core sample to determine fluid saturation, e) injecting a plurality of increasing ratios of said first fluid to said second fluid into said core sample and displacing said first and second fluids from said core sample through a second member that is permeable to both said said first and second fluids to effect a plurality of differing steady-state conditions, f) repeatedly scanning said core sample with X-rays during each of the steady-state conditions in step e) and measuring the attenuation of said X-rays as they pass through said core sample to determine fluid saturation, g) terminating steps e) and f) at 100% first fluid injection into said core sample, h) injecting a plurality of decreasing ratios of said first fluid to said second fluid into said core sample to displace said first and second fluids through said second member to effect a plurality of differing steady-state conditions until a second irreducible first fluid saturation condition is reached, i) repeatedly scanning said core sample with X-rays during each of the steady-state conditions in step h) and measuring the attenuation of said X-rays as they pass through said core sample to determine fluid saturation, j) measuring pressure gradient along said core sample during steps b) through i), and k) determining two-phase, steady-state relative permeability of said first and second fluids in said core sample from said saturation and pressure measurements taken from said core sample during steps b) through i).

10. The method of claim 9 further comprising the steps of:

l) repeating desaturation step (c) in a series of steps for a plurality of varying differential pressures across said core sample, m) repeating X-ray attenuation measurement step (d) for each of the varying differential pressures of step (1) to determine a plurality of fluid saturations, and n) determining capillary pressure of said porous rock by relating said plurality of varying differential pressures to said plurality of fluid saturations.

11. The method of claim 10 wherein each repetition of steps (c)–(d) is carried out at pressure and saturation equilibrium conditions.

* * * * *